(12) United States Patent
Choi

(10) Patent No.: US 11,931,573 B2
(45) Date of Patent: Mar. 19, 2024

(54) MUSCLE STIMULATION APPARATUS AND MUSCLE STIMULATION SYSTEM THEREOF

(71) Applicant: alimolistudio LC., Chuncheon-si (KR)

(72) Inventor: Won Seok Choi, Yongin-si (KR)

(73) Assignee: alimolistudio LC., Chuncheon-si (KR)

( * ) Notice: Subject to any disclaimer, the term of this patent is extended or adjusted under 35 U.S.C. 154(b) by 0 days.

(21) Appl. No.: 17/523,927

(22) Filed: Nov. 11, 2021

(65) Prior Publication Data
US 2023/0133215 A1 May 4, 2023

(30) Foreign Application Priority Data
Nov. 3, 2021 (KR) .................. 10-2021-0149768

(51) Int. Cl.
*A61N 1/04* (2006.01)
*A61N 1/36* (2006.01)

(52) U.S. Cl.
CPC ....... *A61N 1/36034* (2017.08); *A61N 1/0452* (2013.01); *A61N 1/0492* (2013.01)

(58) Field of Classification Search
CPC . A61N 1/36034; A61N 1/0452; A61N 1/0492
See application file for complete search history.

(56) References Cited

U.S. PATENT DOCUMENTS

| | | | |
|---|---|---|---|
| 2006/0217768 A1* | 9/2006 | Buhlmann | A61N 1/36034 607/2 |
| 2016/0022989 A1* | 1/2016 | Pfeifer | A61N 1/36021 604/20 |
| 2020/0206504 A1* | 7/2020 | Jennings | A61N 1/0456 |

FOREIGN PATENT DOCUMENTS

| | | |
|---|---|---|
| CN | 101237906 B | 8/2008 |
| KR | 10-2017-0091935 A | 8/2017 |
| KR | 10-2017-0127581 A | 11/2017 |

OTHER PUBLICATIONS

Non-final Office Action dated Aug. 28, 2023 from the Korean Patent Office for Korean Application No. 10-2021-0149768.

* cited by examiner

*Primary Examiner* — Ankit D Tejani
*Assistant Examiner* — Joshua Brendon Solomon
(74) *Attorney, Agent, or Firm* — Insight Law Group, PLLC; Seung Lee

(57) ABSTRACT

The present disclosure can provide a muscular stimulation apparatus and a system including the same, which apply a voltage through at least one electric stimulation pad that is in close contact with at least one body part of a user, and simultaneously or selectively adjusts a resistance applied to an anode (+) or a cathode (−) of at least one electrode connected to the electric stimulation pad.

7 Claims, 10 Drawing Sheets

FIG. 8

```
const int pMosPins[4] = {2, 4, 6, 8};
const int nMosPins[4] = {3, 5, 7, 9};
const int ve0Pins[4] = {10, 12, A0, A2};
const int ve1Pins[4] = {11, 13, A1, A3};

void setup() {
  int i = 0;
  for(i=0; i<4; i++){
    pinMode(pMosPins[i], OUTPUT);
    pinMode(nMosPins[i], OUTPUT);
    pinMode(ve0Pins[i], OUTPUT);
    pinMode(ve1Pins[i], OUTPUT);
  }
  for(i=0; i<4; i++){
    digitalWrite(pMosPins[i], LOW);
    digitalWrite(nMosPins[i], LOW);
    digitalWrite(ve0Pins[i], HIGH);
    digitalWrite(ve1Pins[i], LOW);
  }
  delay(1);
} void loop() {
  testCon();
} void testCon(){
  digitalWrite(pMosPins[0], HIGH);
  pMosCon(HIGH);
  delayMicroseconds(1000);
  pMosCon(LOW);
  delayMicroseconds(1000);
  nMosCon(HIGH);
  delayMicroseconds(1000);
  nMosCon(LOW);
  delayMicroseconds(1000);
} void pMosCon(bool condition){
  int i = 0;
  for(i=0; i<4; i++){
    digitalWrite(pMosPins[i], condition);
  }
} void nMosCon(bool condition){
  int i = 0;
  for(i=0; i<4; i++){
    digitalWrite(nMosPins[i], condition);
  }
}
```

MUSCLE STIMULATION APPARATUS AND MUSCLE STIMULATION SYSTEM THEREOF

CROSS-REFERENCE TO RELATED APPLICATION

This application claims under 35 U.S.C. § 119(a) the benefit of priority to Korean Patent Application No. 10-2021-0149768 filed on Nov. 3, 2021, the entire contents of which are incorporated herein by reference.

BACKGROUND

(a) Technical Field

The present disclosure relates to a muscular stimulation apparatus, and more specifically, to a muscular stimulation system including the same.

(b) Background Art

Electrical muscular stimulation (EMS) is to apply electrical stimulation to the user's muscle by supplying a current to the user's body through a wire or an electrode and is known to cause skeletal muscle contraction by being variously applied to muscle augmentation through contraction and relaxation of muscles, muscle exercise, incontinence management, and spinal deformity management. In other words, when the body moves, the same current as an electrical command signal sent from the brain to the muscle directly flows into the muscle through a mechanical apparatus to cause the contraction of the motor nerves and muscle fibers and the current flows but there is no feeling of being electrocuted because it is adjusted similar to the signal of the human body.

The electrical muscular stimulation is used for clinical purposes, including the treatment of spinal cord injury patients and stroke patients, the recovery of the motion function of paralyzed extremities, and the prevention of muscle atrophy. For example, such electrical muscular stimulation method includes functional electrical stimulation (FES), which is classified into an invasive method and a non-invasive method according to the method of placement on the skin surface or under the skin of a patient. The invasive method can accurately stimulate each muscle, but cause side effects such as inflammation due to the electrode. On the other hand, the non-invasive method reduces the side effects such as inflammation caused by the electrode but can have difficulty in accurately stimulating the muscles.

To deliver the accurate stimulation to the user's relevant part in this electrical muscular stimulation method, the minimum resistance and the number of electrodes disposed capable of minimizing the patient's skin resistance are important factors.

Therefore, there is a need for a technology capable of removing the side effects such as inflammation due to the electrodes even while delivering accurate stimulation to the user's muscles, etc.

RELATED ART DOCUMENT

Patent Document (Patent Documents 1) Korean Patent Application Laid-Open No. 10-2017-0127581 (Nov. 22, 2017)

SUMMARY OF THE DISCLOSURE

The present disclosure has been made in efforts to solve the above technical problem, and an object of the present disclosure is to provide a muscular stimulation apparatus and a muscular stimulation system including the same, which can remove the loss of the current and the voltage that can be applied to desired muscular parts or the interference of resistance by applying an accurate current or voltage to a point for applying stimulation to a user's body part.

In addition, another object of the present disclosure is to provide a muscular stimulation apparatus and a muscular stimulation system including the same, which can stimulate muscles to be measured by sharing a single electrode in a shape disposed in a direction parallel to the part of the user's body to which stimulation is applied, thereby minimizing the number of electrodes for the muscles to which stimulation is to be applied.

The technical object of the present disclosure are not limited to the aforementioned technical objects, and other technical objects not mentioned can be clearly understood by those skilled in the art to which the present disclosure pertains from the following description.

A muscular stimulation apparatus according to the present disclosure can include a configuration that applies a voltage through at least one electric stimulation pad that is in close contact with at least one body part of a user, and simultaneously or selectively adjusts a resistance generated at an anode (+) or a cathode (−) of at least one electrode connected to the electric stimulation pad.

According to an exemplary embodiment of the present disclosure, the electric stimulation pad can include a structure of being attached in parallel in a long axis direction ("L" direction) along an electric stimulation part with respect to the electric stimulation part among the user's body parts.

According to the exemplary embodiment of the present disclosure, the muscular stimulation apparatus can include a main control unit (micro control unit) configured to control an operation of the apparatus; at least one half H-bridge driver unit (half H-driver unit) configured to simultaneously or selectively apply a current or a voltage input to the electrode; and at least one voltage control unit configured to control the current or the voltage.

According to the exemplary embodiment of the present disclosure, the voltage control unit can include a switch converter formed with at least one voltage regulator or voltage selector that adjusts the current or the voltage.

According to the exemplary embodiment of the present disclosure, the voltage control unit can include a single voltage selector or a multiple voltage selector connected to the half H-bridge driver unit (half H-driver unit).

According to the exemplary embodiment of the present disclosure, the half H-bridge driver unit (half H-driver unit) can include a single IC chip or a multiple gate transistor.

According to the exemplary embodiment of the present disclosure, the electrode can be formed in the number (n) that is the same as or less than the number of user's muscles to be measured.

In addition, the present disclosure provides a muscular stimulation system including the muscular stimulation apparatus, and includes one or more processors;

a memory; and a muscular stimulation apparatus comprising one or more programs, in which the one or more programs are configured to be stored in the memory, and executed by the one or more processors, and the muscular stimulation apparatus can have a configuration of applying a voltage through at least one electric stimulation pad that is in close contact with at least one body part of the user, and simultaneously or selectively adjusting a resistance applied to an anode (+) or a cathode (−) of at least one electrode connected to the electric stimulation pad.

According to an exemplary embodiment of the present disclosure, the electric stimulation pad can include a structure of being attached in parallel in a long axis direction ("L" direction) with respect to an electric stimulation part among the user's body parts.

According to the muscular stimulation apparatus and the muscular stimulation system including the same, it is possible to remove the loss of the current and the voltage that can be applied to undesired muscular parts or the interference of resistance by applying the accurate current or voltage to the point for applying stimulation to the user's body part.

In addition, according to the muscular stimulation apparatus and the muscular stimulation system including the same, it is possible to stimulate muscles to be measured by sharing a single electrode in a shape disposed in a direction parallel to the part of the user's body to which stimulation is applied, thereby minimizing the number of electrodes for the muscles to which stimulation is to be applied.

BRIEF DESCRIPTION OF THE DRAWINGS

FIG. 8 is a diagram showing an experimental coding using the muscular stimulation apparatus according to the exemplary embodiment of the present disclosure.

DETAILED DESCRIPTION

Hereinafter, specific exemplary embodiments of the present disclosure will be described with reference to the drawings. However, this is merely illustrative and the present disclosure is not limited thereto.

However, in the description of the present exemplary embodiment, portions overlapped with other exemplary embodiments will be omitted for more clear and concise description, and the omission of the description does not mean that the portions are excluded from the present disclosure and the scope thereof should be recognized in the same way as in other exemplary embodiments.

In the description of the present disclosure, if it is determined that the detailed description of the known technology related to the present disclosure can unnecessarily obscure the gist of the present disclosure, the detailed description thereof will be omitted. In addition, the terms to be described later are terms defined in consideration of functions in the present disclosure, which can vary depending upon the intentions or customs of users and operators. Therefore, the definitions thereof should be made based on the content throughout the present specification.

The technical spirit of the present disclosure is determined by the claims, and the following exemplary embodiments are only one means for effectively explaining the technical spirit of the present disclosure to those skilled in the art to which the present disclosure pertains.

As described above, the present disclosure can provide a muscular stimulation apparatus and a system including the same, which can minimize the loss of a current or a voltage by delivering accurate stimulation to the user's muscle part in an electrical muscular stimulation method, and also minimize a skin resistance due to the unintentional stimulation applied to the user's muscle part.

To this end, the present disclosure disposes a diode on each of a plurality of NPN transistors and PNP transistors controlled by a microcontroller unit at an output terminal of an EMS or FES device and disposes two diodes on an output terminal of a half H-driver IC, respectively, thereby blocking a leakage current and delivering stimulation to the number of electrodes corresponding to the muscles.

Figure 1:
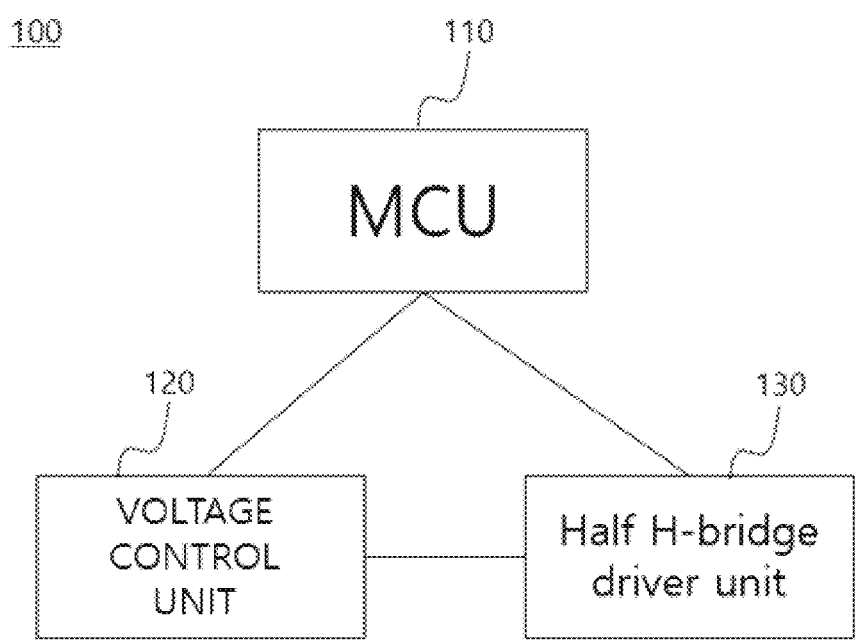
FIG. 1 is a configuration diagram of a muscular stimulation apparatus according to an exemplary embodiment of the present disclosure.
Figure 9:
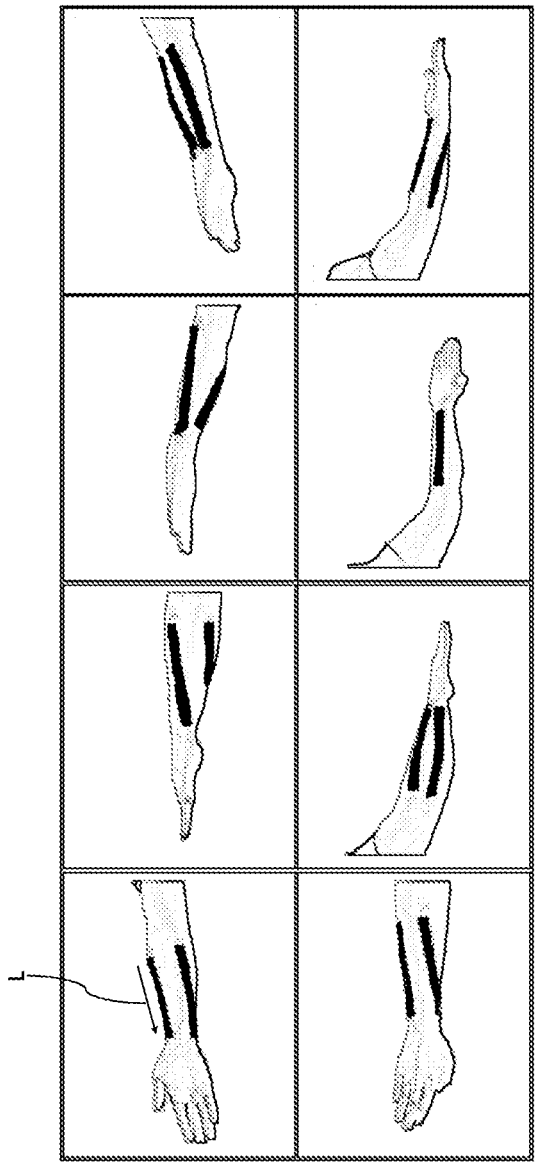
FIG. 9 is pictures showing the states where electrical stimulation pads of the muscular stimulation apparatus according to the exemplary embodiment of the present disclosure are attached.

FIG. 1 is a block diagram showing a configuration of a muscular stimulation apparatus according to an exemplary embodiment of the present disclosure, and FIG. 9 is pictures showing a state where an electrical stimulation pad of the muscular stimulation apparatus according to the exemplary embodiment of the present disclosure is attached.

Referring to FIGS. 1 and 9, a muscular stimulation apparatus 100 according to an exemplary embodiment of the present disclosure is configured to include a main control unit (micro control unit) 110 configured to control an operation of the apparatus, a plurality of half H-bridge driver units (half H-driver unit) 130 configured to simultaneously or selectively apply a current or a voltage input to an electrode (not shown), and a plurality of voltage control units 120 configured to control the current or the voltage.

The muscular stimulation apparatus 100 can provide electrical stimulation to the user's muscles using the muscular stimulation pad. Specifically, the muscular stimulation apparatus 100 can provide electrical stimulation to the user using an electrical stimulation method using functional electrical stimulation (FES), electrical muscular stimulation (EMS), and transcutaneous electrical nerve stimulation (TENS).

The muscular stimulation apparatus 100 according to the present disclosure applies a voltage through a plurality of electrical stimulation pads (not shown) that are in close contact with the user's body part, that is, the muscle, and allows resistances applied to anodes (+) or cathodes (−) of the plurality of electrodes connected to the electrical stimulation pads to be simultaneously or selectively adjusted, thereby minimizing the loss of the voltage or the current and the user's skin resistance.

The main control unit (micro control unit) 110 can control an operation of the voltage control unit 120 configured to control the current or voltage provided by the muscular stimulation apparatus 100, and control the current or the voltage to be selectively provided to the half H-bridge driver unit 130.

The voltage control unit 120 is not specially limited as long as it is a configuration capable of adjusting the current or the voltage, and for example, can be a switch converter formed with a plurality of voltage regulators or voltage selectors capable of adjusting the current or the voltage. The voltage control unit 120 can be configured as a single voltage selector or a multiple voltage selector connected to the half H-bridge driver unit 130.

The half H-bridge driver unit 130 can include a single IC chip or a multi-gate transistor.

In other words, the voltage control unit 120 and the half H-bridge driver unit 130 according to the present disclosure can have a structure in which one voltage selector is connected to the anodes (+) or the cathodes (−) of the plurality of half H-bridge driver units 130 or the plurality of voltage selectors are connected to the anode (+) or the cathode (−) of one haft H-bridge driver unit 130.

The muscular stimulation pad can provide electrical stimulation to the user in response to an input of the muscular stimulation apparatus 100. The muscular stimulation pad can be connected to the muscular stimulation apparatus 100 by a wire or wirelessly, and attached to or worn on the user's body to provide electrical stimulation to the user's body corresponding to the electrical stimulation waveform determined by the muscular stimulation apparatus 100.

A muscular stimulation pad 32 can include a plurality of electrodes configured to apply electrical stimulation to the user's body. Here, the electrode can be formed of an anode, a cathode, an electric wire, and an insulator for separating the anode and the cathode.

Here, according to the present disclosure, the muscular stimulation pad can be disposed in a form of being attached in the longitudinal direction, that is, along a long axis direction (L) around the muscle to be measured among the user's body parts. In some cases, the muscular stimulation pad can be formed in a shape of surrounding the muscle part to be measured. At this time, the number of electrodes of the muscular stimulation pad can be provided in the number (n) that is the same as or less than the number of muscles to be measured. For example, as shown in FIG. 9, the muscular stimulation pad is an example of disposing the electrodes that stimulate the muscles of the user's right forearm, and a total of four can be disposed to stimulate the muscles of the inside, outside, and both sides of the arm, respectively.

Figure 2:
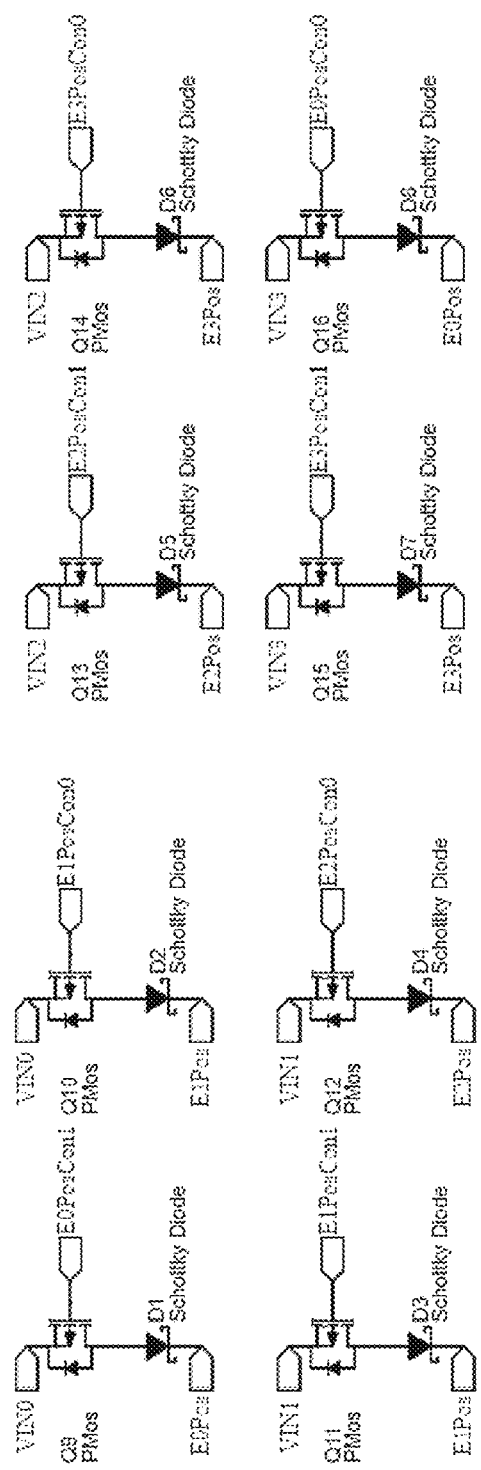
FIG. 2 is a diagram showing a voltage selector of the muscular stimulation apparatus according to the exemplary embodiment of the present disclosure.
Figure 3:
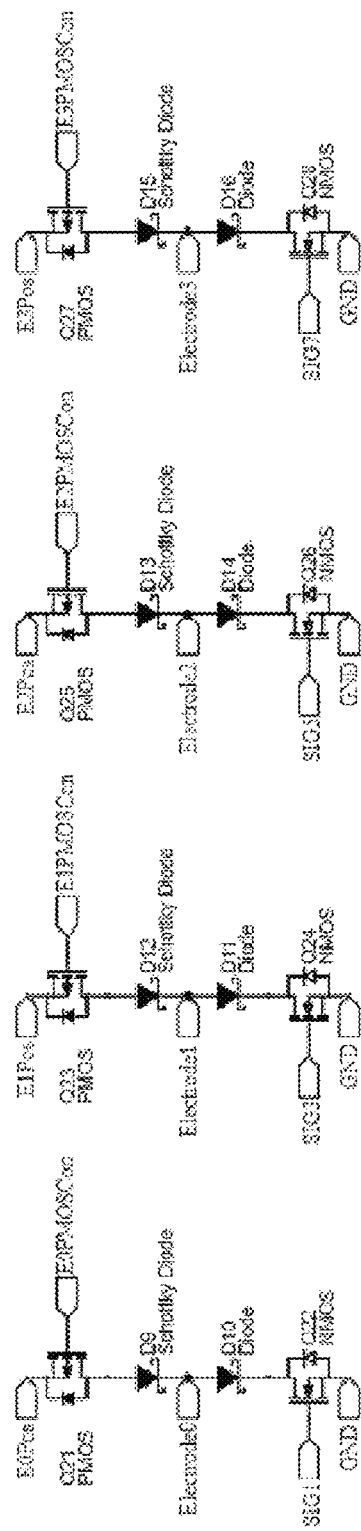
FIG. 3 is a diagram showing a half H-bridge driver unit of the muscular stimulation apparatus according to the exemplary embodiment of the present disclosure.

FIG. 2 is a diagram showing a voltage selector of the muscular stimulation apparatus according to the exemplary embodiment of the present disclosure, and FIG. 3 is a diagram showing a half H-bridge driver unit of the muscular stimulation apparatus according to the exemplary embodiment of the present disclosure.

Referring to FIGS. 2 and 3, as shown in FIG. 2, the voltage selector of the muscular stimulation apparatus 100 according to the present disclosure can be controlled so that each voltage input value is selectively applied to any one or one or more of anodes of the plurality of half H-bridge driver units 130 through the main control unit 110. For example, VIN0 can be supplied to one or both of the anodes of the half H-bridge driver units 0, 1 (E0Pos, E1Pos).

Therefore, for the circuit consisting of the voltage selector and the half H-bridge driver unit 130, it is possible to adjust the polarity of the connected electrodes and to simultaneously or selectively change the resistance values of the electrodes, thereby preventing the unnecessary loss of the currents applied to the electrodes.

In addition, as described above, the voltage control unit 120 and the half H-bridge driver unit 130 can have a structure in which one voltage selector is connected to the anodes (+) or cathodes (−) of the plurality of half H-bridge driver units 130, or the plurality of the voltage selectors are connected to the anode (+) or cathode (−) of one half H-bridge driver unit 130. Therefore, high-resistance or low-resistance can be controlled to be simultaneously or selectively applied to the anodes (+) or cathodes (−) of the half H-bridge driver units 130.

In other words, in one example, as shown in FIG. 3, the four half H-bridge driver units 130 can control the P-MOSFETs connected to the electrodes through SIG0, SIG2, SIG4, and SIG6 having even-numbered signals, and control the N-MOSFET through SIG1, SIG3, SIG5, and SIG7 having odd-numbered signals. Here, the P-MOSFET and the N-MOSFET can be connected to the electrodes through switching diodes to block the function of a parasitic diode and prevent an undesired reverse current.

Therefore, the muscular stimulation apparatus 100 according to the present disclosure can be configured to stimulate two or more muscles using one electrode while minimizing the unnecessary loss of the current or the voltage to the user's muscles to be measured. Therefore, it is possible to induce the contraction of muscles even with the number of electrodes that is the same as or less than the number of muscles to which stimulation is to be applied.

Figure 4:
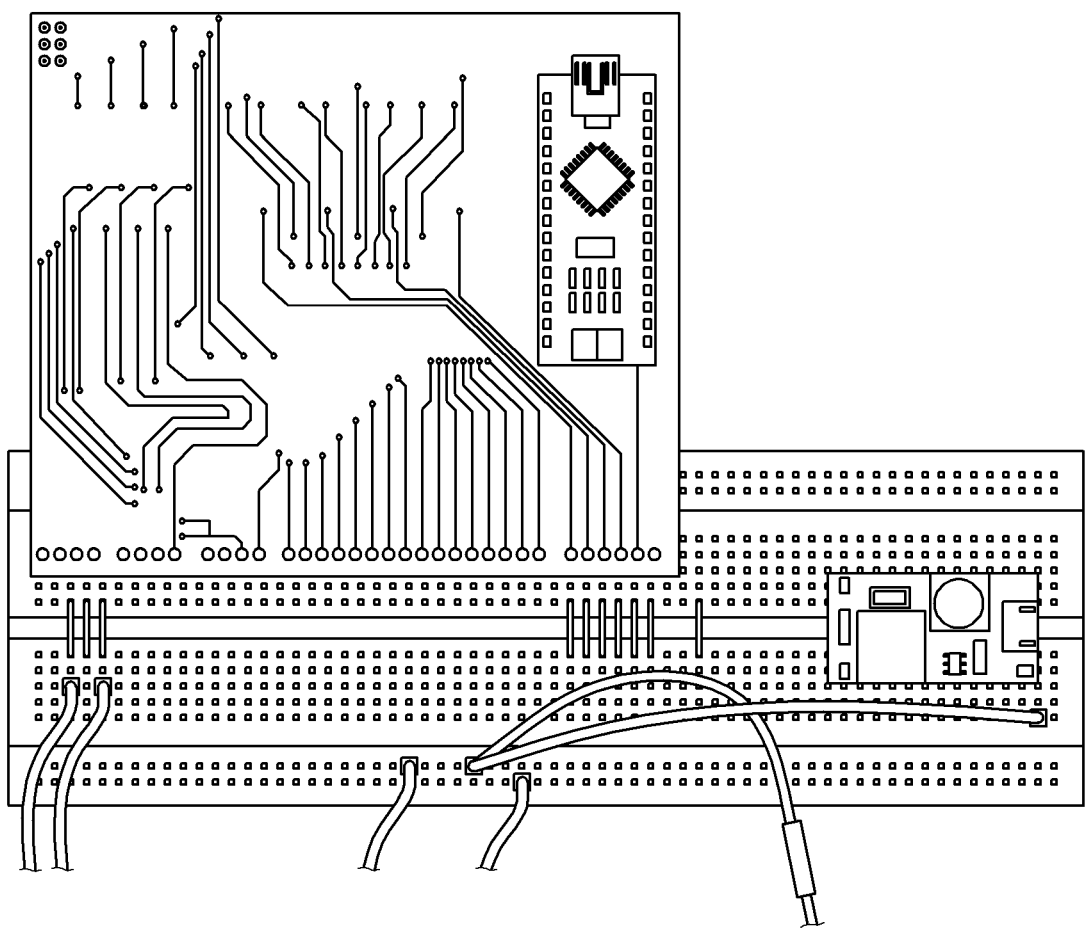
FIGS. 4 and 5 are pictures showing a test circuit of the muscular stimulation apparatus according to the exemplary embodiment of the present disclosure.
Figure 5:
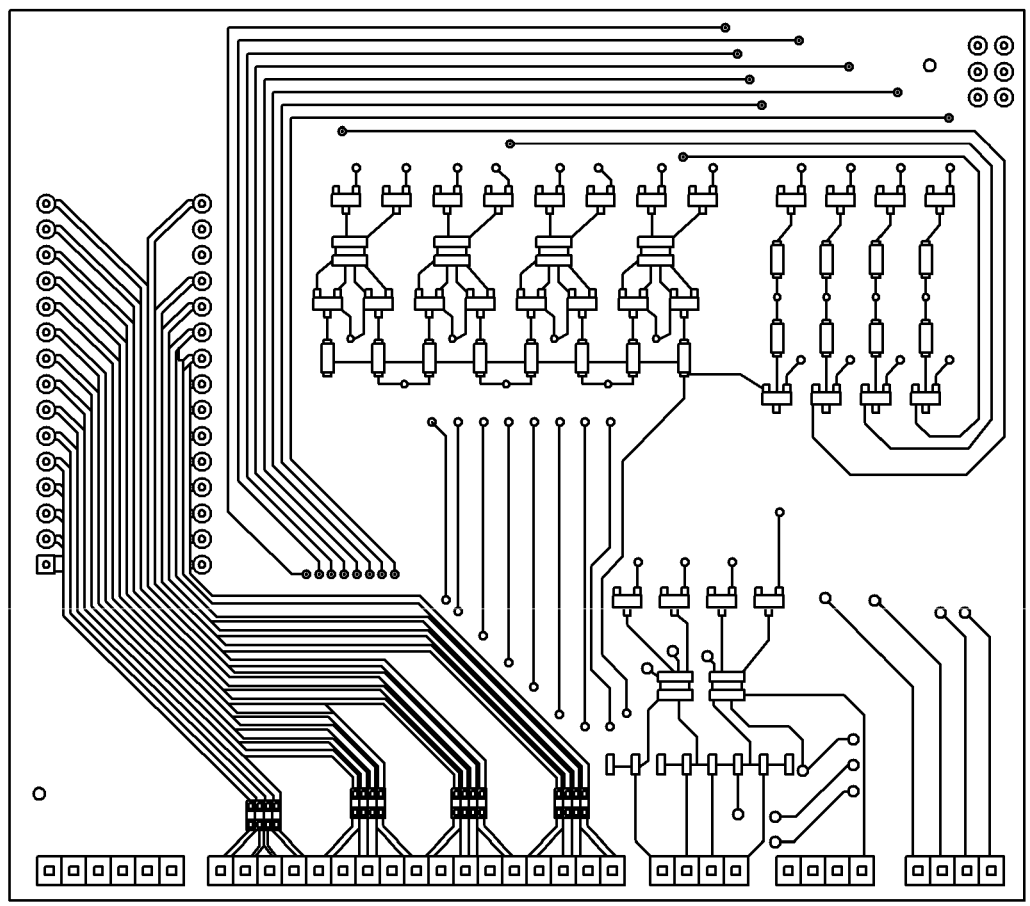
Figure 6:
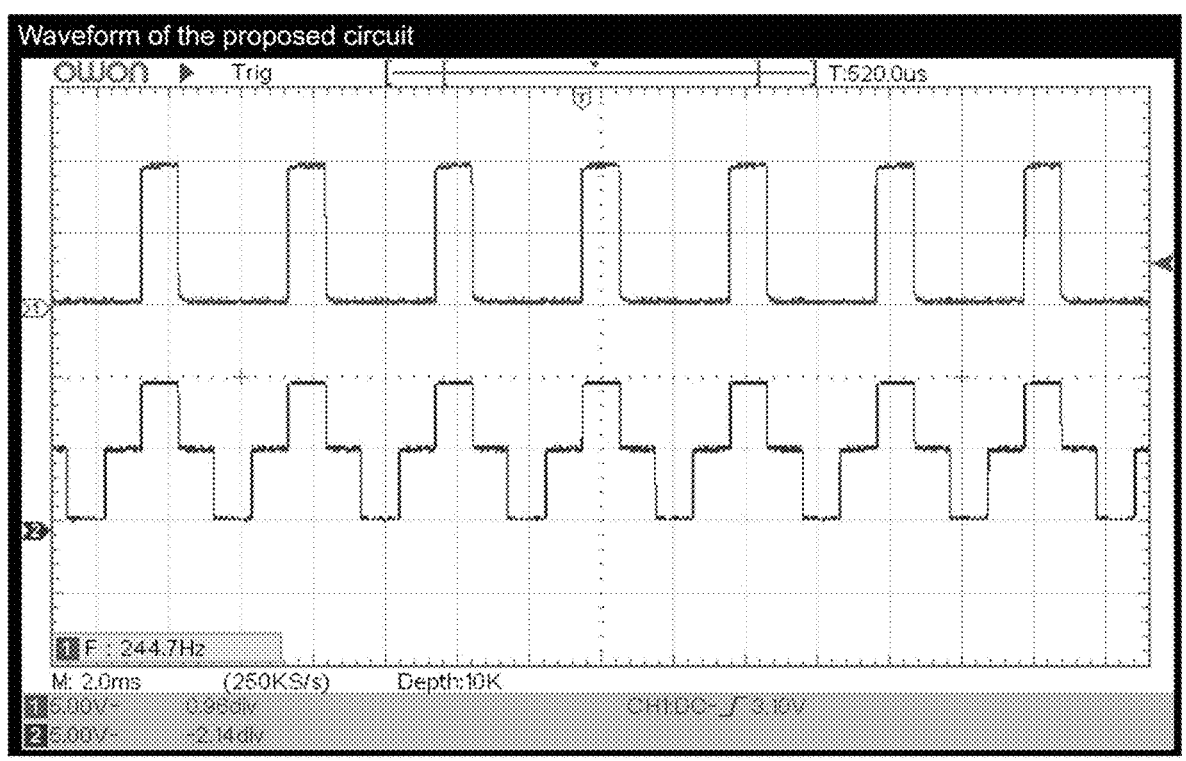
FIGS. 6 and 7 are diagrams showing experimental values representing waveforms of a circuit using the muscular stimulation apparatus according to the exemplary embodiment of the present disclosure.
Figure 7:
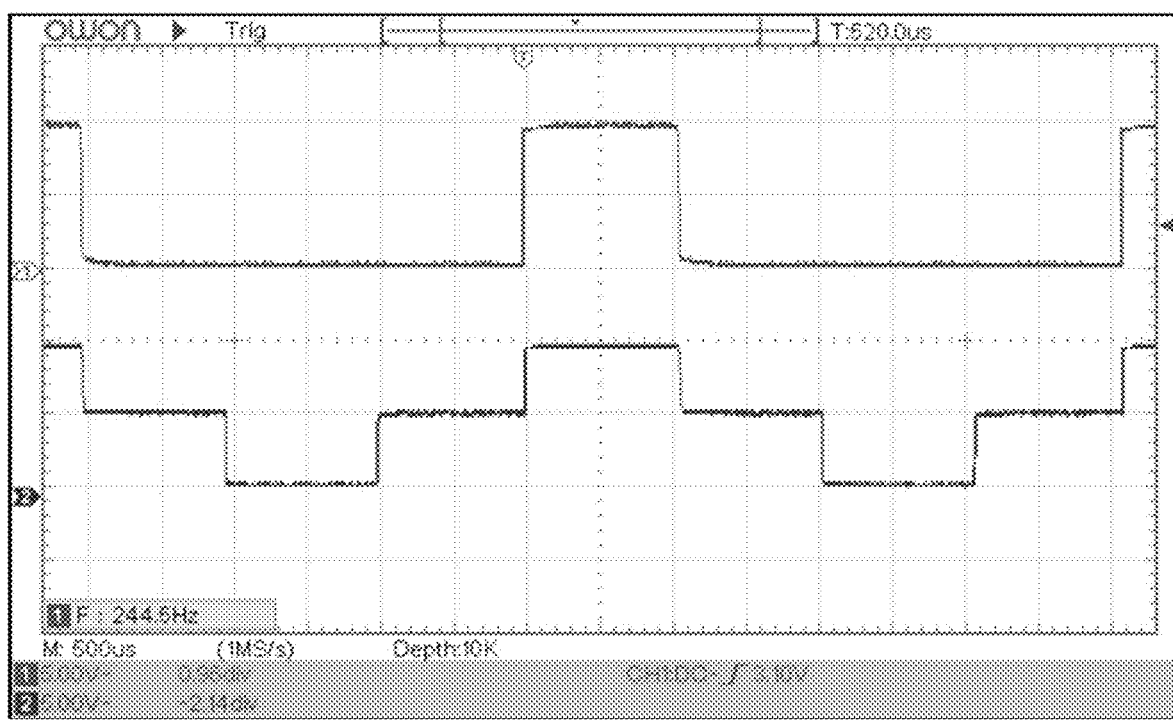

Hereinafter, describing a voltage application test result using the muscular stimulation apparatus 100 according to the present disclosure with reference to the drawings, FIGS. 4 and 5 are pictures showing a test circuit of the muscular stimulation apparatus according to an embodiment of the present disclosure, FIGS. 6 and 7 are diagrams showing experimental values representing waveforms of a circuit using the muscular stimulation apparatus according to the exemplary embodiment of the present disclosure, and FIG. 8 is a diagram showing an experimental coding using the muscular stimulation apparatus according to the exemplary embodiment of the present disclosure.

Referring to FIGS. 4 to 8, a method for designing a sample circuit shown in FIGS. 4 and 5 to code and input a computer program shown in FIG. 8 and then apply an actual voltage to measure a waveform in response thereto was performed to deliver a voltage using the aforementioned muscular stimulation apparatus 100 according to the present disclosure.

Here, the test method was conducted in a testing circuit gerber file method, and conducted by preparing a PCB according to Table 1 below, and setting a controller under the following experimental conditions.

TABLE 1

|  | Base Material | PCB Layers | PCB thickness | Surface Finish | Outer copper weight |
|---|---|---|---|---|---|
| PCB | FR-4 | 2 | 1.6 mm | HASL (with lead) | 1 oz |

Controller setting:
Controller: Arduino Nano(ATMEGA328p) 16 Mhz
IDE: Arduino IDE 1.8.2
Input Voltage: 10 V According to the experimental results, as shown in FIGS. 6 and 7, the duty cycle of 25% and the period of the pulse with a waveform of 2 ms were measured in the circuit prepared as described above. Therefore, it can be confirmed that according to the circuit of the muscular stimulation apparatus 100 according to the present disclosure, it is possible to minimize the stimulation of the user's muscles to be measured.

Figure 10:
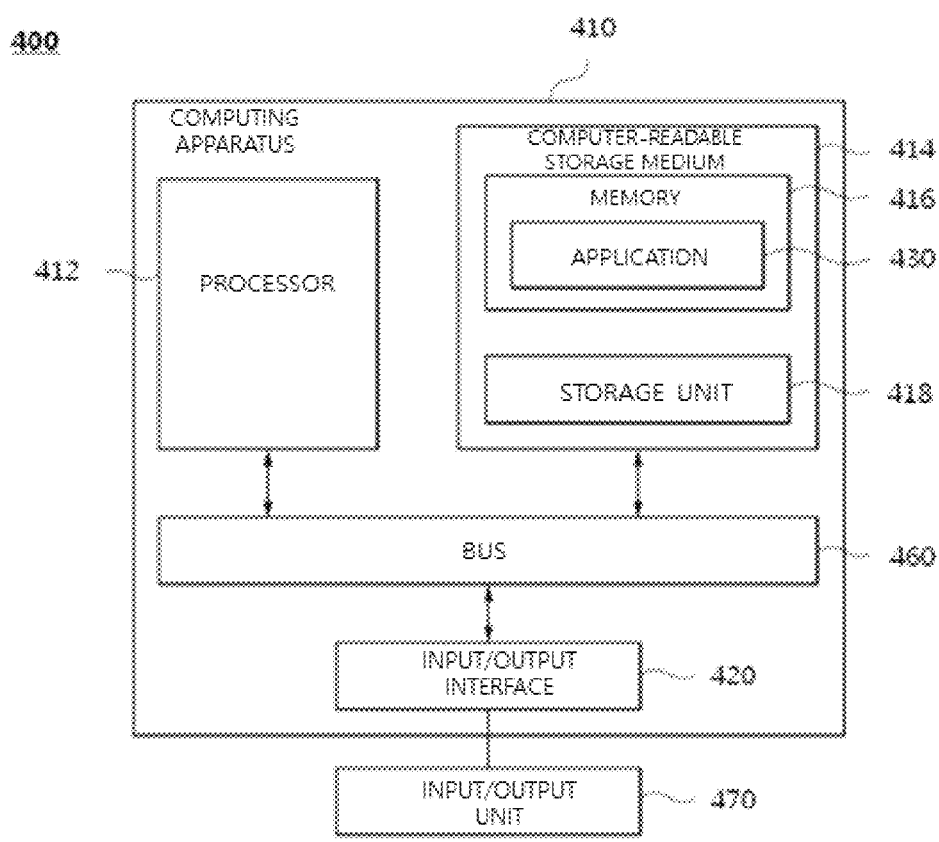
FIG. 10 shows a computing environment including an exemplary computing apparatus suitable for use in exemplary embodiments.

Meanwhile, FIG. 10 shows a computing environment including an exemplary computing apparatus suitable for use in exemplary embodiments.

An exemplary computing environment 400 shown in FIG. 10 includes a computing apparatus 410. Generally, each configuration can have different functions and capabilities, and additionally include components suitable for the configuration, even if not described below. The computing apparatus 410 can be the aforementioned muscular stimulation apparatus 100 configured to stimulate the muscles.

The computing apparatus 410 includes at least one processor 412, a computer readable storage medium 414, and a bus 460. The processor 412 is coupled to the bus 460, and the bus 460 connects various other components of the computing apparatus 410 to the processor 412, including a computer-readable storage medium 414.

The processor 412 can allow the computing apparatus 410 to operate according to the aforementioned exemplary embodiment. For example, the processor 412 can execute computer-executable instructions stored in the computer-readable storage medium 414, and when executed by the processor 412, the computer-executable instructions stored in the computer-readable storage medium 414 can be configured to allow the computing apparatus 410 to perform operations according to a predetermined exemplary embodiment.

The computer-readable storage medium 414 can be configured to store computer-executable instructions or program codes (e.g., instructions included in application 430), program data (e.g., data used by the application 430), and/or other information in a suitable form. The application 430 stored in the computer-readable storage medium 414 includes a predetermined set of instructions executable by the processor 412.

A memory 416 and a storage unit 418 shown in FIG. 10 are examples of the computer-readable storage medium 414. The computer-executable instructions executable by the processor 412 can be loaded in the memory 416. In addition, program data can be stored in the memory 416. For example, the memory 416 can be a volatile memory, a non-volatile memory, or a suitable combination thereof, such as a random access memory. As another example, the storage unit 418 can include one or more detachable or non-detachable components for storing information. For example, the storage unit 418 can be a hard disk, a flash memory, a magnetic disk, an optical disk, other forms of storage media that can be accessed by the computing apparatus 410 and can store desired information, or a suitable combination thereof.

The computing apparatus 410 can also include one or more input/output interfaces 420 configured to provide interfaces for one or more input/output units 470. The input/output interface 420 is connected to the bus 460. The input/output unit 470 can be connected to (other components of) the computing apparatus 410 through the input/output interface 420. The input/output unit 470 includes an input unit such as a pointing unit, a keyboard, a touch input unit, a voice input unit, a sensor unit, and/or a photographing unit and/or an output unit such as a display unit, a printer, a speaker, and/or a network card.

Although the representative exemplary embodiments of the present disclosure have been described above in detail, those skilled in the art to which the present disclosure pertains will understand that the aforementioned exemplary embodiment can be variously modified without departing from the scope of the present disclosure. Therefore, the scope of the present disclosure should not be limited to the aforementioned exemplary embodiments, but should be determined not only by the claims to be described later but also those equivalent to the claims.

What is claimed is:

1. A muscular stimulation apparatus,
wherein the muscular stimulation apparatus applies a voltage through at least one electric stimulation pad that is in close contact with at least one body part of a user, and
adjusts a resistance generated at an anode (+) or a cathode (−) of at least one electrode connected to the electric stimulation pad,
wherein the muscular stimulation apparatus comprises:
a main control unit (micro control unit) configured to control an operation of the apparatus;
at least one half H-bridge driver unit (half H-driver unit) configured to simultaneously or selectively apply a current or a voltage input to the electrode; and
at least one voltage control unit configured to control the current or the voltage,
wherein the voltage control unit comprises: a switch converter formed with at least one voltage regulator or voltage selector that adjusts the current or the voltage,
wherein the voltage control unit and the half H-bridge driver unit have a structure in which one voltage selector is connected to the anodes (+) or cathodes (−) of the plurality of half H-bridge driver units, or the plurality of the voltage selectors are connected to the anode (+) or cathode (−) of one half H-bridge driver unit.

2. The muscular stimulation apparatus of claim 1,
wherein the electric stimulation pad is attached in parallel in a long axis direction ("L" direction) along an electric stimulation part with respect to the electric stimulation part among the user's body parts.

3. The muscular stimulation apparatus of claim 1,
wherein the voltage control unit comprises: a single voltage selector or a multiple voltage selector connected to the half H-bridge driver unit (half H-driver unit).

4. The muscular stimulation apparatus of claim 1,
wherein the half H-bridge driver unit (half H-driver unit) comprises: a single IC chip or a multiple gate transistor.

5. The muscular stimulation apparatus of claim 1,
wherein the electrode is formed in the number (n) that is the same as or less than the number of user's muscles to be measured.

6. A system comprising:
one or more processors;
a memory; and
a muscular stimulation apparatus comprising one or more programs,
wherein the one or more programs are configured to be stored in the memory, and executed by the one or more processors, and
wherein the muscular stimulation apparatus comprises:
a main control unit (micro control unit) configured to control an operation of the apparatus;
at least one half H-bridge driver unit (half H-driver unit) configured to simultaneously or selectively apply a current or a voltage input to the electrode; and
at least one voltage control unit configured to control the current or the voltage, wherein the muscular stimulation apparatus applies a voltage through at least one electric stimulation pad that is in close contact with at least one body part of the user, and simultaneously or selectively adjusts a resistance applied to an anode (+) or a cathode (−) of at least one electrode connected to the electric stimulation pad, wherein the voltage control unit comprises: a switch converter formed with at least one voltage regulator or voltage selector that adjusts the current or the voltage, wherein the voltage control unit and the half H-bridge driver unit have a structure in which one voltage selector is connected to the anodes (+) or cathodes (−) of the plurality of half H-bridge driver units, or the plurality of the voltage selectors are connected to the anode (+) or cathode (−) of one half H-bridge driver unit.

7. The system of claim 6, wherein the electric stimulation pad comprises: a structure of being attached in parallel in a long axis direction ("L" direction) with respect to an electric stimulation part among the user's body parts.

\* \* \* \* \*